US010155123B2

(12) United States Patent
Mukawa et al.

(10) Patent No.: US 10,155,123 B2
(45) Date of Patent: Dec. 18, 2018

(54) NEUTRON CAPTURE THERAPY SYSTEM

(71) Applicants: SUMITOMO HEAVY INDUSTRIES, LTD., Tokyo (JP); Kyoto University, Kyoto (JP)

(72) Inventors: Tetsuya Mukawa, Kanagawa (JP); Kazuya Taki, Kanagawa (JP); Hiroki Tanaka, Kyoto (JP)

(73) Assignees: SUMITOMO HEAVY INDUSTRIES, LTD., Tokyo (JP); KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 15/957,605

(22) Filed: Apr. 19, 2018

(65) Prior Publication Data

US 2018/0236265 A1   Aug. 23, 2018

Related U.S. Application Data

(63) Continuation of application No. PCT/JP2016/081913, filed on Oct. 27, 2016.

(30) Foreign Application Priority Data

Oct. 29, 2015  (JP) .................................. 2015-212993

(51) Int. Cl.
*A61N 5/10*  (2006.01)
*G01T 1/29*  (2006.01)

(52) U.S. Cl.
CPC ............. *A61N 5/1048* (2013.01); *A61N 5/10* (2013.01); *A61N 5/103* (2013.01); *A61N 5/1077* (2013.01);
(Continued)

(58) Field of Classification Search
USPC ...................................................... 250/518.1
See application file for complete search history.

(56) References Cited

U.S. PATENT DOCUMENTS 5,410,575 A   4/1995  Uhm
5,433,693 A   7/1995  Ott
(Continued)

FOREIGN PATENT DOCUMENTS

EP   1 658 878 A    5/2006
EP   2 805 745 A1  11/2014
(Continued)

OTHER PUBLICATIONS

Kononov et al., "Optimization of an accelerator-based epithermal neutron source for neutron capture therapy", Applied Radiation and Isotopes 61, 2004, pp. 1009-1013.*
(Continued)

*Primary Examiner* — Phillip A Johnston
(74) *Attorney, Agent, or Firm* — Michael Best & Friedrich LLP (57) ABSTRACT

A neutron capture therapy system includes a neutron beam irradiation unit that applies neutron beams, a treatment table on which an irradiation object irradiated with the neutron beams is mounted, a storage unit that stores distribution data indicating a distribution of hydrogen atoms or nitrogen atoms of a part to be irradiated of the irradiation object, a gamma ray detection unit that detects gamma rays generated from the irradiation object due to irradiation with the neutron beams, and a neutron flux distribution calculation unit that calculates a distribution of neutron flux in the irradiation object on the basis of the distribution data stored in the storage unit and gamma ray distribution data detected by the gamma ray detection unit.

4 Claims, 6 Drawing Sheets

(52) U.S. Cl.
CPC .......... *G01T 1/29* (2013.01); *A61N 2005/109* (2013.01); *A61N 2005/1087* (2013.01)

(56) References Cited

U.S. PATENT DOCUMENTS

| | | | |
|---|---|---|---|
| 6,423,972 B1 * | 7/2002 | Fehrenbacher | G01T 3/08 250/370.05 |
| 6,674,829 B1 * | 1/2004 | Skold | A61N 5/10 250/492.1 |
| 7,514,694 B2 * | 4/2009 | Stephan | G01T 3/00 250/390.01 |
| 7,663,119 B2 * | 2/2010 | Sved | G01T 3/00 250/390.01 |
| 8,126,243 B2 | 2/2012 | Hamada et al. | |
| 8,481,951 B2 | 7/2013 | Jongen et al. | |

FOREIGN PATENT DOCUMENTS

| | | |
|---|---|---|
| EP | 2 979 728 A1 | 2/2016 |
| JP | H09-500286 A | 1/1997 |
| JP | 2004-233168 A | 8/2004 |
| JP | 2014-195505 A | 10/2014 |
| JP | 2014-228401 A | 12/2014 |
| WO | WO-94/015670 A1 | 7/1994 |
| WO | WO-2007/023723 A1 | 3/2007 |
| WO | WO-2010/000857 A1 | 1/2010 |

OTHER PUBLICATIONS

International Search Report issued in Application No. PCT/JP2016/081913, dated Jan. 24, 2017.
Search Report issued in European Patent Application No. 16859912.4, dated Oct. 18, 2018.

* cited by examiner

NEUTRON CAPTURE THERAPY SYSTEM

RELATED APPLICATIONS

Priority is claimed to Japanese Patent Application No. 2015-212993, filed Oct. 29, 2015, and International Patent Application No. PCT/JP2016/081913, the entire content of each of which is incorporated herein by reference.

BACKGROUND

Technical Field

A certain embodiment of the present invention relates to a neutron capture therapy system.

Description of Related Art

In the related art, in a neutron capture therapy system, there is a method disclosed in the related art as a method for measuring neutrons. In a neutron capture therapy system disclosed in the related art, a gold wire or the like is disposed on a surface of an irradiation object, and neutrons are measured afterwards on the basis of radiation data of the gold wire. There is also a method of directly measuring neutrons with a neutron monitor.

SUMMARY

According to an embodiment of the present invention, there is provided a neutron capture therapy system including a neutron beam irradiation unit that applies neutron beams; a treatment table on which an irradiation object irradiated with the neutron beams is mounted; a storage unit that stores distribution data indicating a distribution of hydrogen atoms or nitrogen atoms of a part to be irradiated of the irradiation object; a gamma ray detection unit that detects gamma rays generated from the irradiation object due to irradiation with the neutron beams; and a neutron flux distribution calculation unit that calculates a distribution of neutron flux in the irradiation object on the basis of the distribution data stored in the storage unit and gamma ray distribution data detected by the gamma ray detection unit.

DETAILED DESCRIPTION

Here, as disclosed in the related art, in the method of measuring neutrons by using a gold wire, measurement can be performed only afterwards, and, since a gold wire is disposed on only a surface of an irradiation object, neutrons inside the irradiation object cannot be measured. In the method of measuring neutrons with a neutron monitor, only neutrons around a surface of an irradiation object can be measured. As mentioned above, neutron flux inside an irradiation object cannot be measured in real time, and thus there is a problem in that it cannot be understood whether or not a neutron beam is applied to the inside of the irradiation object as planned for treatment.

It is desirable to provide a neutron capture therapy system in which it can be understood whether or not a neutron beam is applied to the inside of an irradiation object as planned for treatment.

Here, a hydrogen atom or a nitrogen atom in the irradiation object reacts with neutron so as to generate a gamma ray from the inside of the irradiation object. In other words, it is possible to specify neutron flux in the irradiation object by specifying detected gamma rays, and hydrogen atoms or nitrogen atoms. Therefore, in the neutron capture therapy system according to the present invention, the neutron flux distribution calculation unit can calculate a distribution of neutron flux in the irradiation object on the basis of the distribution data indicating a distribution of hydrogen atoms or nitrogen atoms of a part to be irradiated of the irradiation object, stored in the storage unit, and gamma ray distribution data detected by the gamma ray detection unit. Since the gamma ray detection unit can detect the gamma rays in real time, the neutron flux distribution calculation unit can calculate a distribution of neutron flux in real time. Consequently, the calculation result is compared with the distribution of neutron flux related to a treatment plan, and thus it is possible to check whether or not neutron beams are applied to the inside of the irradiation object as planned for treatment.

In the neutron capture therapy system, the gamma ray detection unit may be formed of a plurality of cameras, and axes of the plurality of cameras may intersect each other. In this case, the gamma ray detection unit can detect gamma rays generated in the irradiation object in a three-dimensional manner.

In the neutron capture therapy system, in a case where a distribution of neutron flux calculated by the neutron flux distribution calculation unit has changed to exceed a range which is predefined on the basis of a distribution of neutron flux set in a treatment plan, the neutron beam irradiation unit may stop irradiation with the neutron beams. Here, in a case where actual irradiation with the neutron beams is different from that in a treatment plan, treatment may be stopped.

The neutron capture therapy system may further include a display unit that displays a distribution of neutron flux calculated by the neutron flux distribution calculation unit. In this case, a user of the system can visually recognize the distribution of neutron flux in the irradiation object in real time.

Hereinafter, a description will be made of an embodiment of the present invention with reference to the drawings. In description of the drawings, the same constituent element is given the same reference numeral, and repeated description will be omitted.

Figure 1:
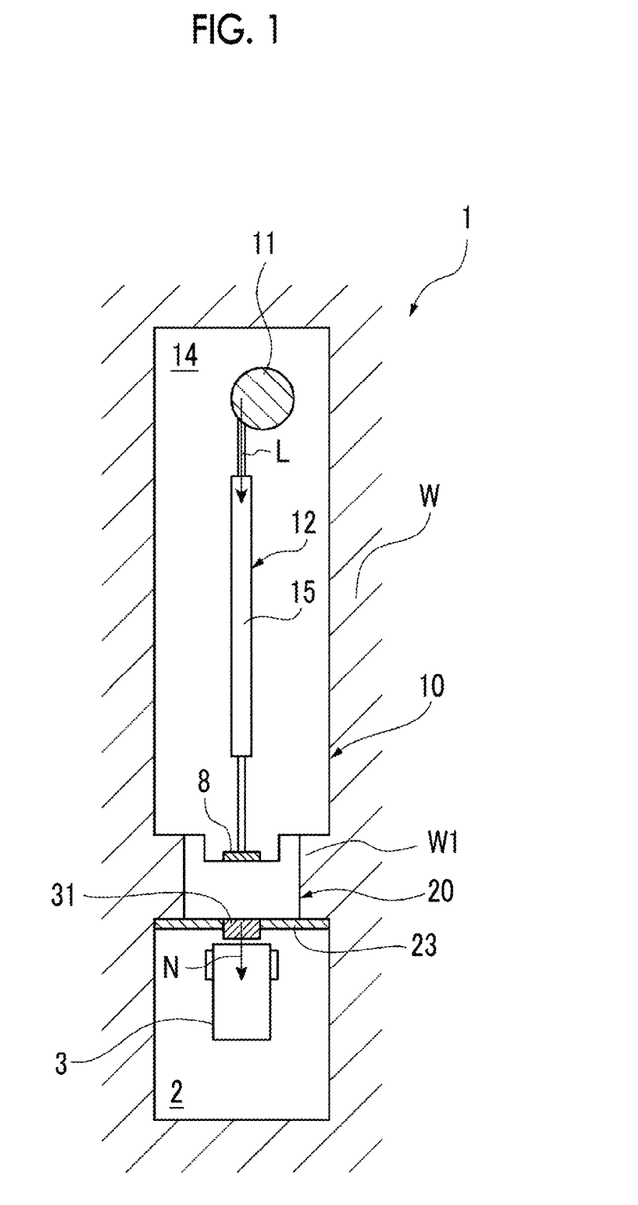
FIG. 1 is a diagram illustrating an arrangement in a neutron capture therapy system according to an embodiment of the present invention.
Figure 2:
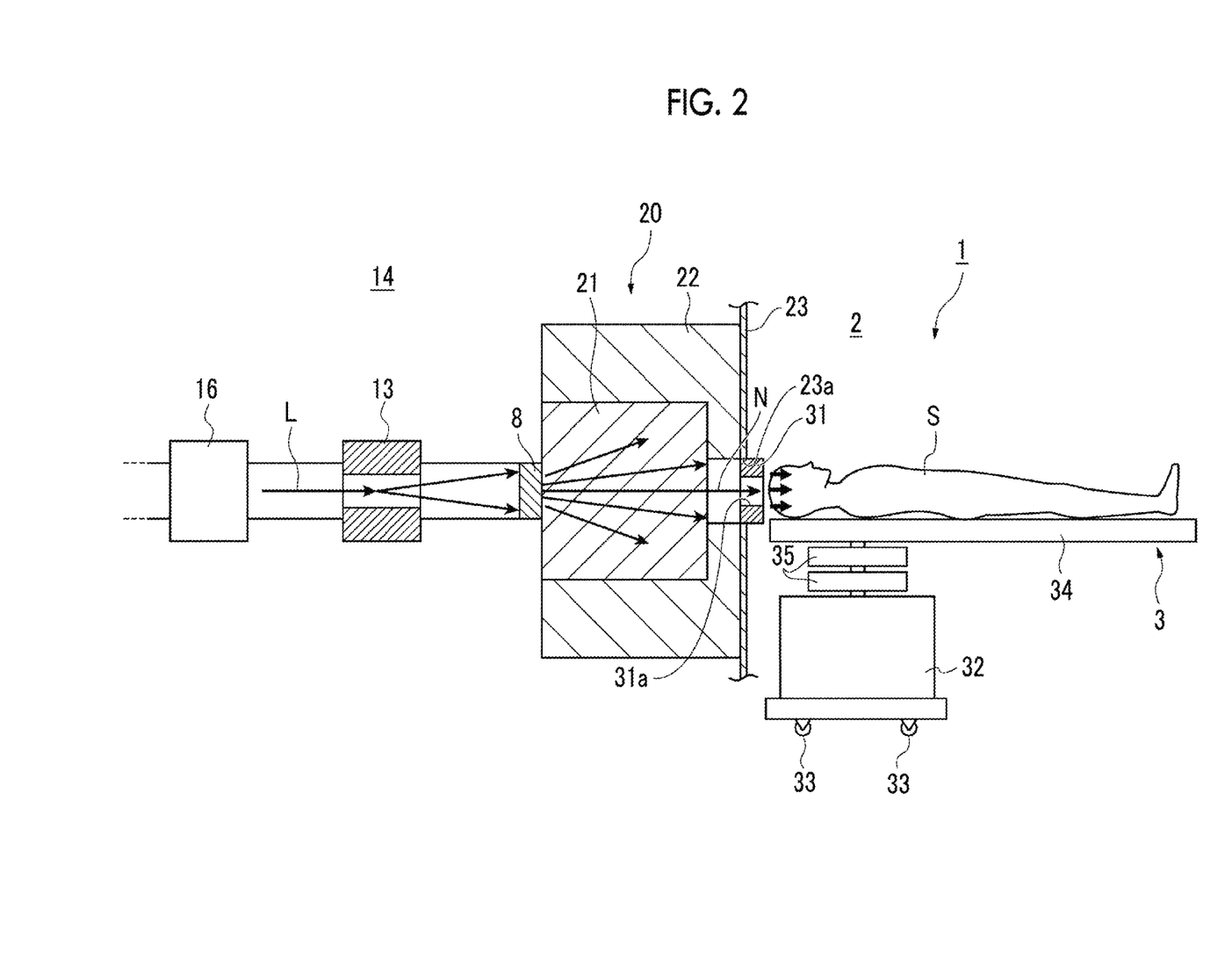
FIG. 2 is a diagram illustrating the periphery of a neutron beam irradiation unit in the neutron capture therapy system in FIG. 1.

First, with reference to FIGS. 1 and 2, a description will be made of a summary of a neutron capture therapy system according to a first embodiment. As illustrated in FIGS. 1 and 2, a neutron capture therapy system 1 performing cancer treatment by using boron neutron capture therapy is a system which performs cancer treatment by irradiating a part (part to be irradiated) into which boron is integrated in a patient (irradiation object) S administrated with boron (10B) with neutron beams. The neutron capture therapy system 1 has an irradiation room 2 in which the patient S constrained to a treatment table 3 is irradiated with a neutron beam N such that cancer treatment for the patient S is performed.

Preparation work such as constraining the patient S to the treatment table 3 is performed in a preparation room (not illustrated) other than the irradiation room 2, and the treatment table 3 to which the patient S is constrained is moved from the preparation room to the irradiation room 2. The neutron capture therapy system 1 includes a neutron beam generation unit 10 which generates neutron beams N for treatment, and a neutron beam irradiation unit 20 which irradiates the patient S constrained to the treatment table 3 in the irradiation room 2 with the neutron beams N.

The neutron beam generation unit 10 includes an accelerator 11 which generates a charged particle beam L, a beam transport path 12 along which the charged particle beam L generated by the accelerator 11 is transported, a charged particle beam irradiation portion 13 which applies the charged particle beam L and controls irradiation of a target 8 with the charged particle beam L, and a current monitor 16 which measures a current of the charged particle beam L, and the target 8 which is irradiated with the charged particle beam L. The accelerator 11 and the beam transport path 12 are disposed inside a charged particle beam generation chamber 14 having a substantially rectangular shape, and the charged particle beam generation chamber 14 is a closed space covered with a concrete shield wall W. The charged particle beam irradiation portion 13 controls, for example, an irradiation position of the target 8 with the charged particle beam L, and the current monitor 16 measures a current of the charged particle beam L applied to the target 8. The charged particle beam irradiation portion 13 and the current monitor 16 may be omitted.

The accelerator 11 accelerates charged particles such as hydrogen ions so as to generate the charged particle beam L such as a proton beam. In the present embodiment, a cyclotron is used as the accelerator 11. The cyclotron has the capability of generating the charged particle beam L of, for example, 60 kW (=30 Mev×2 mA). As the accelerator 11, instead of the cyclotron, other accelerators such as a synchrotron, a synchrocyclotron, or a linac may be used.

One end of the beam transport path 12 is connected to the accelerator 11. The beam transport path 12 is provided with a beam adjustment portion 15 adjusting the charged particle beam L. The beam adjustment portion 15 includes a horizontal steering electromagnet and a horizontal-vertical steering electromagnet adjusting an axis of the charged particle beam L, a quadrupole electromagnet suppressing divergence of the charged particle beam L, a four-way slit shaping the charged particle beam L, and the like. The beam transport path 12 may have a function of transporting the charged particle beam L, and the beam adjustment portion 15 may be omitted.

The charged particle beam L transported along the beam transport path 12 is subject to an irradiation position in the charged particle beam irradiation portion 13, and is then applied to the target 8. The charged particle beam irradiation portion 13 may be omitted such that the same location of the target 8 is normally irradiated with the charged particle beam L.

The target 8 is irradiated with the charged particle beam L so as to generate the neutron beams N. The target 8 is made of, for example, beryllium (Be), lithium (Li), tantalum (Ta), or tungsten (W), and has a plate shape. The target 8 is not limited to a plate shape, and may have other shapes (for example, a liquid). The neutron beams N generated by the target 8 are applied to the patient S in the irradiation room 2 by the neutron beam irradiation unit 20.

The neutron beam irradiation unit 20 includes a deceleration member 21 which decelerates the neutron beams N emitted from the target 8 and a shield member 22 which blocks radiations such as the neutron beams N and gamma rays from being emitted outward, and the deceleration member 21 and the shield member 22 form a moderator.

The deceleration member 21 has, for example, a laminate structure formed of a plurality of different materials, and materials of the deceleration member 21 are appropriately selected according to all conditions such as energy of the charged particle beam L. Specifically, for example, in a case where an output from the accelerator 11 is a proton beam of 30 MeV, and a beryllium target is used as the target 8, materials of the deceleration member 21 may be lead, iron, aluminum, and calcium fluoride.

The shield member 22 is provided to surround the deceleration member 21, and has a function of blocking radiations such as the neutron beams N and gamma rays generated due to generation of the neutron beams N from being emitted outward of the shield member 22. At least a part of the shield member 22 is buried in a wall W1 separated from the charged particle beam generation chamber 14 and the irradiation room 2. The shield member 22 may not be buried in the wall W1. A wall body 23 forming a part of a sidewall surface of the irradiation room 2 is provided between the irradiation room 2 and the shield member 22. A collimator attachment portion 23a which is an outlet of the neutron beams N is provided on the wall body 23. A collimator 31 adjusting an irradiation field of the neutron beams N is fixed to the collimator attachment portion 23a.

In the neutron beam irradiation unit 20, the charged particle beam L is applied to the target 8, and thus the target 8 generates the neutron beams N. The neutron beams N generated by the target 8 is decelerated when passing through the deceleration member 21, and the neutron beams N emitted from the deceleration member 21 pass through the collimator 31 and are applied to the patient S on the treatment table 3. Here, as the neutron beams N, thermal neutron beams or epithermal neutron beams with relatively low energy may be used.

The treatment table 3 functions as a mounting table used for neutron capture therapy, and is movable from the preparation room (not illustrated) to the irradiation room 2 in a state of being mounted with the patient S. The treatment table 3 includes a base portion 32 forming a base of the treatment table 3, casters 33 which enable the base portion 32 to be moved on a floor surface, a top plate 34 on which the patient S is mounted, and a drive portion 35 which relatively moves the top plate 34 for the base portion 32. The base portion 32 may be fixed to the floor without using the casters 33.

Figure 3:
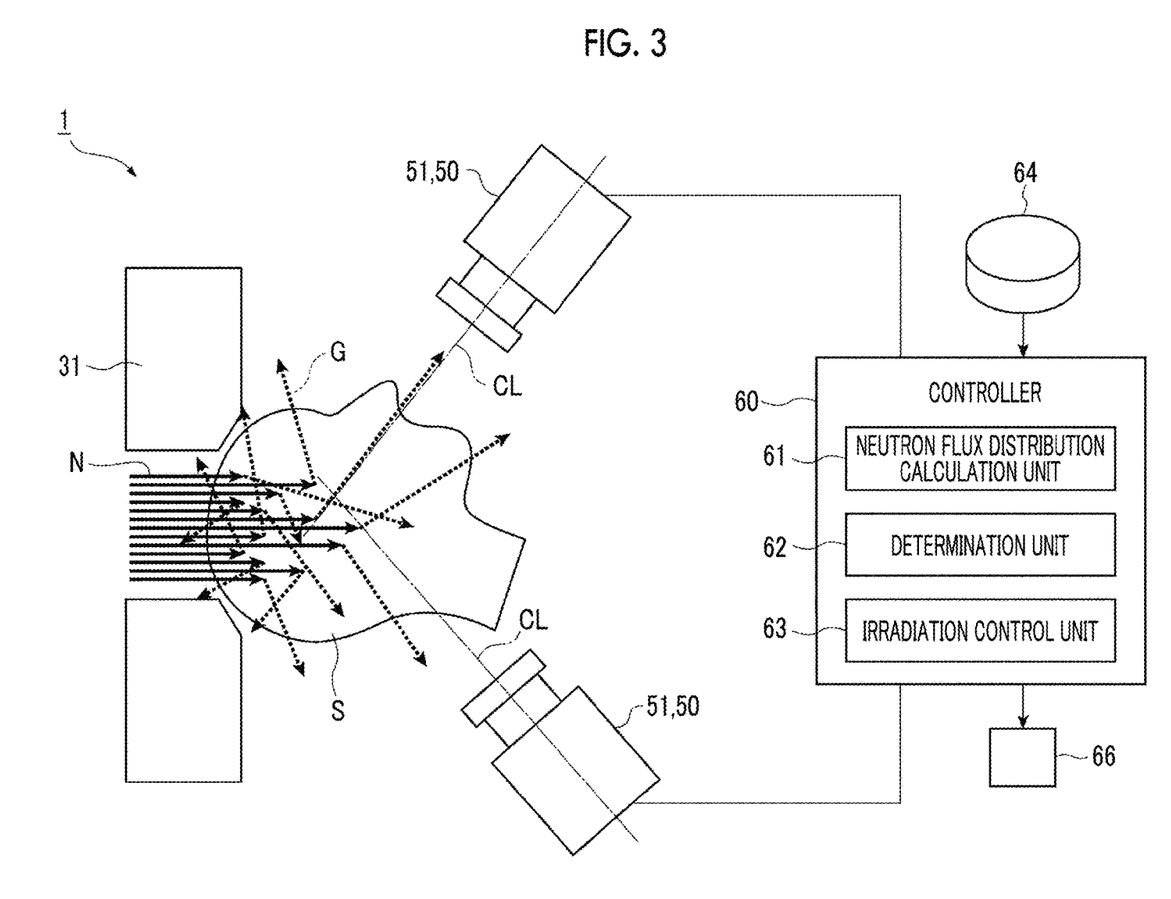
FIG. 3 is a diagram illustrating main constituent elements of the neutron capture therapy system according to the embodiment of the present invention.

Next, with reference to FIG. 3, main constituent elements of the neutron capture therapy system 1 according to the present embodiment will be described. As illustrated in FIG. 3, the neutron capture therapy system 1 includes a storage unit 64, a gamma ray detection unit 50, a controller 60, and a display unit 66.

The storage unit 64 stores distribution data indicating a distribution of hydrogen atoms or nitrogen atoms of an affected part of the patient S. The storage unit 64 may store both distribution data of hydrogen atoms and distribution data of nitrogen atoms. The distribution data is stored during treatment planning in a preliminary stage in which neutron beams are applied by the neutron capture therapy system 1 according to the present embodiment. The distribution data may be obtained by using hydrogen atom density or nitrogen atom density of each region of the inside of the patient S on the basis of a computed tomography (CT) image of the patient S. Alternatively, a distribution of hydrogen atoms may be directly acquired on the basis of a magnetic resonance imaging (MRI) image. The storage unit 64 outputs the stored distribution data to the controller 60 at a necessary timing. The storage unit 64 may store various pieces of data.

Figure 6:
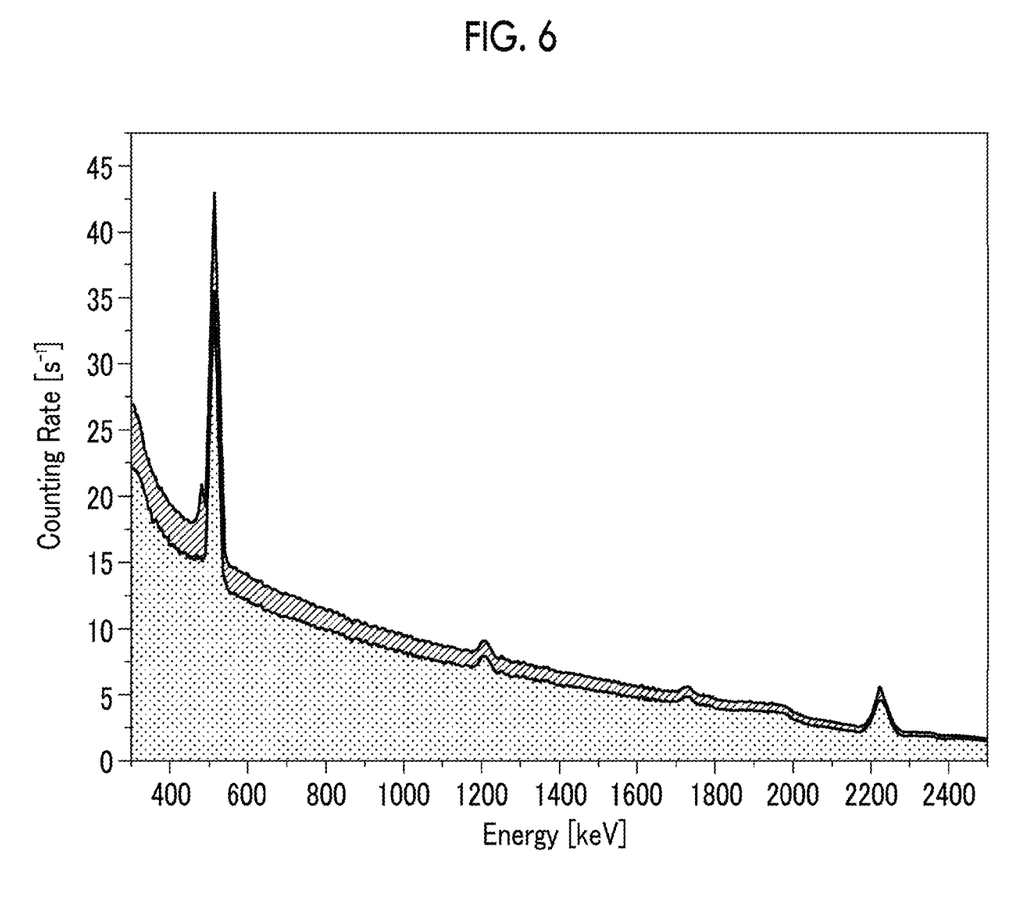
FIG. 6 is a graph illustrating an example of an energy distribution of gamma rays in a predetermined location, detected by a gamma ray detection unit.

The gamma ray detection unit 50 detects gamma rays G generated from the patient S as a result of irradiation with the neutron beams N. Hydrogen and nitrogen which are distributed in a human body in a large amount have a large neutron reaction sectional area, and thus emit gamma rays with high energy due to reaction. Therefore, the gamma ray detection unit 50 can detect the gamma rays G generated from the inside of the patient S due to irradiation with the neutron beams N. The hydrogen atoms react with neutron so as to emit the gamma rays G of 2.2 MeV. The nitrogen atoms react neutron so as to emit the gamma rays G of 10.8 MeV. For example, FIG. 6 illustrates an example of an energy distribution of the gamma rays G in a predetermined location, detected by the gamma ray detection unit 50. As illustrated in FIG. 6, a peak at 2.2 MeV increases in a location including a lot of hydrogen atoms.

The gamma ray detection unit 50 is formed of a plurality of cameras 51. Axes CL of the plurality of the cameras 51 intersect each other. Here, the "axis" indicates a virtual axis passing through the center of a detectable range of each camera 51. In the present embodiment, an intersection angle is set to 90°, but other angles (for example, 60° or 150°) may be set. Directions of the respective cameras 51 are set such that a portion in which the respective Axes CL intersect each other (or a portion in which the axes are closest to each other) are disposed inside an affected part of the patient S mounted on the treatment table 3. A state in which the axes CL of the plurality of cameras 51 intersect each other includes a state in which the axes CL have a torsional positional relationship. Each camera 51 is disposed at a position which is separated from the outlet of the collimator 31 at a predetermined distance and is separated from the affected part of the patient S mounted on the treatment table 3 on the periphery of the treatment table 3. The axis CL of each camera 51 is directed toward the affected part (herein, the head) of the patient S mounted on the treatment table 3. Each camera 51 may be fixed at a defined position, but may be moved around the patient S through connection to a movement mechanism. The cameras 51 may be attached to the treatment table 3, may be attached to the wall body 23, and may be attached to a separately provided stand specific to the cameras 51. In the present embodiment, the number of provided cameras 51 may be two, and may be three or more. Each camera 51 outputs a detection result to the controller 60.

The controller 60 has a function of controlling the entire operation of the neutron capture therapy system 1, and is formed of, for example, a CPU, a ROM, and a RAM. The controller 60 has a neutron flux distribution calculation unit 61, a determination unit 62, and an irradiation control unit 63. The controller 60 may perform control during treatment planning in a preliminary stage of performing treatment using neutron beams and control during treatment using neutron beams. During treatment planning, the controller 60 may perform a process of setting a region of interest (ROI) on the basis of a CT image or an MRI image, and may also determine a composition of each ROI. The controller 60 may acquire distribution data of hydrogen atoms or nitrogen atoms in each ROI. The controller 60 may perform treatment simulation using, for example, Monte Carlo simulation, so as to acquire a distribution of neutron flux for the affected part of the patient S. The controller 60 may perform the simulation from a plurality of irradiation directions. The controller 60 determines an irradiation direction optimal for treatment on the basis of a plurality of simulation results. Such a process during treatment planning may be performed by a processing unit other than the controller 60. Treatment simulation is not limited to the Monte Carlo simulation, and other simulations may be performed.

The neutron flux distribution calculation unit 61 calculates a distribution of neutron flux in the patient S on the basis of the distribution data of hydrogen atoms or nitrogen atoms stored in the storage unit 64 and the gamma ray distribution data detected by the gamma ray detection unit 50. Specifically, the neutron flux distribution calculation unit 61 calculates a distribution of neutron flux by using the following Equations (1), (2) and (3). In the following equations, "r" indicates the detection efficiency in the gamma ray detection unit 50, "ϕ" indicates thermal neutron flux, "σ" indicates a nuclear reaction sectional area, and "N" indicates density of the number of atoms. The detection efficiency and the nuclear reaction sectional area are preset values. The nuclear reaction sectional area indicates an amount of gamma rays generated per neutron. Equations (1), (2) and (3) are examples of equations in a case where a distribution of neutron flux is calculated on the basis of hydrogen atoms, and similar equations may also be used in a case where calculation is performed on the basis of nitrogen atoms.

$$P_{(x,y,z)} = r \times \phi_{n(x,y,z)} \times \sigma_{(^1H(n,\gamma))} \times N_{^1H_{(x,y,z)}} \quad (1)$$

$$N_{^1H_{(x,y,z)}} \quad (2)$$

$$\phi_{n(x,y,z)} = \frac{P_{(x,y,z)}}{r \times \sigma_{(^1H(x,\gamma))} \times N_{^1H_{(x,y,z)}}} \quad (3)$$

P(x,y,z) on the left side of Equation (1) indicates a distribution of gamma rays in each location of the affected part of the patient S corresponding to xyz coordinates, and may be obtained on the basis of a detection result in the gamma ray detection unit 50. P(x,y,z) is a value which changes in real time during irradiation with neutron beams. Equation (2) indicates a distribution of hydrogen atoms in each location of the affected part of the patient S corresponding to xyz coordinates, and may be obtained on the basis of the distribution data acquired from the storage unit 64. Equation (3) for calculating ϕ(x,y,z) indicating a distribution of neutrons in each location of the affected part of the patient S corresponding to xyz coordinates is obtained by using simultaneous equations of Equations (1) and (2). ϕ(x,y,z) may be calculated in real time by assigning each value to the right side of Equation (3).

The determination unit 62 determines whether or not the distribution of neutron flux calculated by the neutron flux distribution calculation unit 61 has changed to exceed a range which is predefined on the basis of a distribution of neutron flux set in a treatment plan. The irradiation control unit 63 controls irradiation with neutron beams in the neutron beam irradiation unit 20. The irradiation control unit 63 performs control such that the neutron beam irradiation unit 20 stops irradiation with neutron beams on the basis of determination in the determination unit 62.

Specifically, in a case where the determination unit 62 determines that the distribution of neutron flux calculated by the neutron flux distribution calculation unit 61 has changed to exceed a range which is predefined on the basis of a distribution of neutron flux set in a treatment plan, the irradiation control unit 63 stops irradiation with neutron beams. For example, in a case where the distribution of neutron flux calculated by the neutron flux distribution calculation unit 61 becomes different from a distribution of neutron flux set in a treatment plan by a predetermined extent or more due to positional deviation of the patient S or a shape change of a neutron beam, irradiation with neutron beams is stopped. In a case where irradiation with neutron beams is stopped, the accelerator 11 stops emitting the charged particle beam L. The "predefined range" indicates an allowable range of a difference between a distribution of neutron flux calculated by the neutron flux distribution calculation unit 61 and a distribution of neutron flux set during treatment planning, and the extent of the range is not particularly limited.

The display unit 66 displays the distribution of neutron flux calculated by the neutron flux distribution calculation unit 61. The display unit 66 receives a calculation result output from the neutron flux distribution calculation unit 61 of the controller 60, and displays the calculation result in real time. The display unit 66 is formed of a monitor and the like.

Next, with reference to a flowchart of FIG. 4, a description will be made of a treatment method using the neutron capture therapy system 1 according to the present embodiment. S10 to S40 in the flowchart correspond to processes of a treatment plan in a preliminary stage in which the patient S is actually irradiated with neutron beams, and S50 to S90 correspond to processes in which treatment is performed by actually irradiating the patient S with neutron beams. The processes in S10 to S40 will be described as being performed by the controller 60, but may be performed a processing device other than the controller 60.

First, the controller 60 sets an ROI on the basis of a CT image of an affected part of the patient S (step S10). Next, the controller 60 determines a composition of each ROI set in S10 (step S20). In this case, the controller 60 acquires distribution data indicating a distribution of hydrogen atoms or nitrogen atoms in each ROI. The controller 60 stores the acquired data in the storage unit 64.

The controller 60 performs treatment simulation related to irradiation of the affected part of the patient S with neutron beams (step S30). Specifically, the controller 60 may perform Monte Carlo simulation as an example of treatment simulation. Consequently, for example, data indicating a distribution of neutron flux as illustrated in FIG. 5 is obtained. The controller 60 performs the simulation with respect to a plurality of irradiation directions. Therefore, a plurality of pieces of data (hereinafter, for description, the data will be referred to as "treatment plan data") indicating a distribution of neutron flux is obtained. The controller 60 determines an irradiation direction optimal for treatment on the basis of the plurality of pieces of treatment plan data indicating the distributions of neutron flux obtained in S30 (step S40). In S40, the controller 60 selects treatment plan data with which the affected part of the patient S can be most appropriately treated from among the plurality of pieces of treatment plan data indicating the distributions of neutron flux, and employs an irradiation direction in the selected treatment plan data.

Next, the irradiation control unit 63 of the controller 60 applies the neutron beams N from the irradiation direction determined in S40, and starts treatment for the affected part of the patient S (step S50). During the treatment, the gamma ray detection unit 50 detects the gamma rays G generated from the inside of the patient S due to irradiation with the neutron beams N in real time, and the controller 60 acquires the detection result (step S60). The neutron flux distribution calculation unit 61 of the controller 60 calculates a distribution of neutron flux in the patient S on the basis of the distribution data of hydrogen atoms or nitrogen atoms stored in the storage unit 64 and the gamma ray distribution data acquired in S60 (step S70). In this case, the neutron flux distribution calculation unit 61 of the controller 60 displays the calculated distribution of neutron flux on the display unit 66.

The determination unit 62 of the controller 60 determines whether or not the distribution of neutron flux calculated in S70 has changed to exceed a range which is predefined on the basis of the treatment plan data indicating the distribution of neutron flux obtained in S30 (step S80). In S80, the determination unit 62 also determines whether or not the treatment is finished. In S80, in a case where the determination unit 62 determines that the distribution of neutron flux calculated in S70 does not change to exceed the range which is predefined on the basis of the treatment plan data, and the treatment is not finished either, the processes from S60 are repeatedly performed.

On the other hand, in S80, in a case where the determination unit 62 determines that the distribution of neutron flux calculated in S70 has changed to exceed the range which is predefined on the basis of the treatment plan data, and/or the treatment is finished, the irradiation control unit 63 stops irradiation with the neutron beams N (step S90). After the stopping, the process illustrated in the flowchart of FIG. 4 is finished.

Next, a description will be made of advantageous effects of the neutron capture therapy system 1 according to the present embodiment.

Here, a hydrogen atom or a nitrogen atom in the patient S reacts with neutron so as to generate a gamma ray from the inside of the patient S. In other words, it is possible to specify neutron flux in the patient S by specifying detected gamma rays, and hydrogen atoms or nitrogen atoms in the patient S. Therefore, in the neutron capture therapy system 1 according to the present embodiment, the neutron flux distribution calculation unit 61 can calculate a distribution of neutron flux in the patient S on the basis of the distribution data indicating a distribution of hydrogen atoms or nitrogen atoms of an affected part of the patient S, stored in the storage unit 64, and gamma ray distribution data detected by the gamma ray detection unit 50. Since the gamma ray detection unit 50 can detect the gamma rays G in real time, the neutron flux distribution calculation unit 61 can calculate a distribution of neutron flux in real time. Consequently, the calculation result is compared with the distribution of neutron flux related to a treatment plan, and thus it is possible to check whether or not neutron beams are applied to the inside of the patient as planned for treatment.

In the neutron capture therapy system 1 according to the present embodiment, the gamma ray detection unit 50 is formed of a plurality of cameras 51, and the axes CL of the plurality of cameras 51 intersect each other. In this case, the gamma ray detection unit 50 can detect the gamma rays G generated in the patient S in a three-dimensional manner without rotating the cameras 51 centering on the patient S. In a case where the camera 51 is rotated (or rotationally moved) centering on the patient S, a mechanism for the operation is necessary. There is no sufficient space between a patient, and the moderator and the treatment table 3, and thus the mechanism may be hard to provide. A neutron beam distribution around the patient may not be obtained as planned for treatment due to disorder of neutron caused by rotation of the camera 51 around the patient. In other words, a neutron flux distribution in the patient's body may not also be obtained as planned for treatment. Therefore, since the gamma ray detection unit 50 is formed of a plurality of cameras 51, the cameras 51 are not rotated, and thus three-dimensional detection of the gamma rays G can be performed without causing the above-described problems. However, a mechanism rotating (or rotationally moving) the camera 51 centering on the patient S may be provided.

In the neutron capture therapy system 1 according to the present embodiment, in a case where a distribution of neutron flux calculated by the neutron flux distribution calculation unit 61 has changed to exceed a range which is predefined on the basis of a distribution of neutron flux set in a treatment plan, the neutron beam irradiation unit 20 may stop irradiation with the neutron beams N. Here, in a case where actual irradiation with the neutron beams N is different from that in a treatment plan, treatment may be stopped.

The neutron capture therapy system 1 according to the present embodiment may further include the display unit 66 which displays a distribution of neutron flux calculated by the neutron flux distribution calculation unit 61. In this case, a user of the system can visually recognize the distribution of neutron flux in the patient S in real time.

The present invention is not limited to the above-described embodiment.

Figure 4:
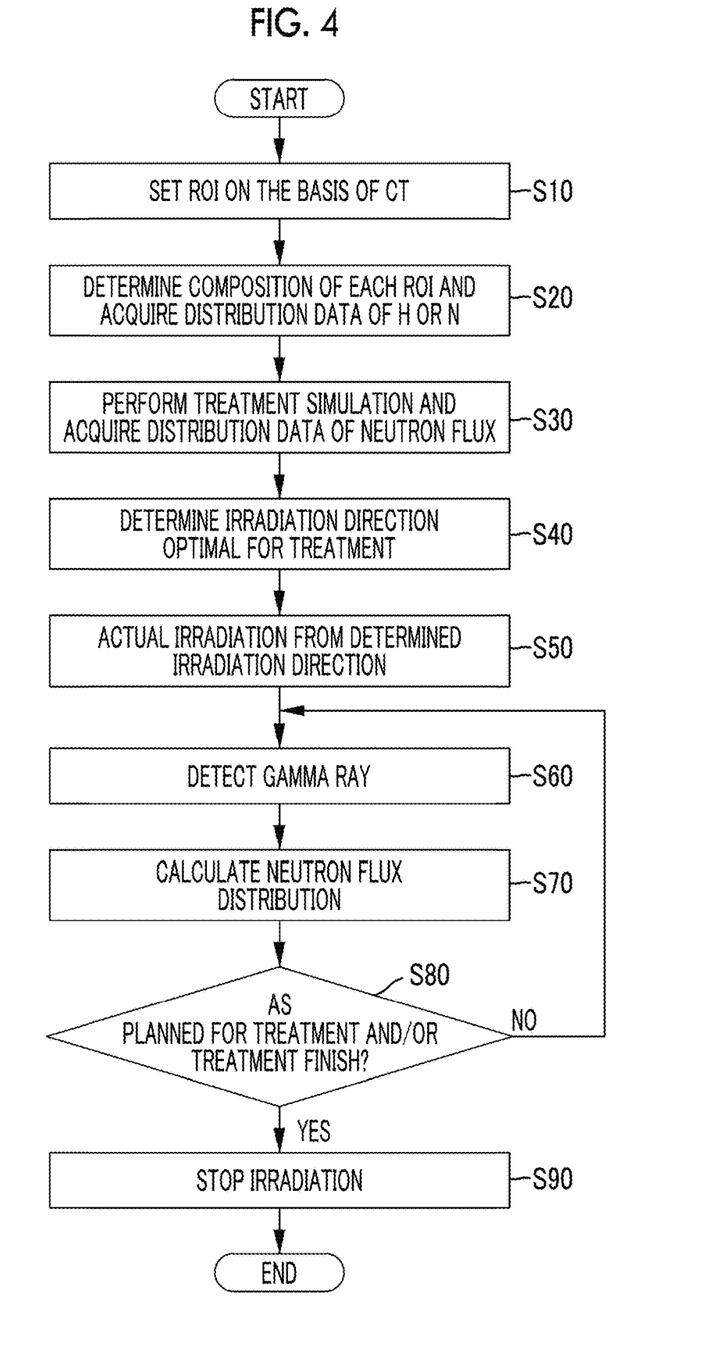
FIG. 4 is a flowchart illustrating procedures of a treatment method using the neutron capture therapy system according to the embodiment of the present invention.
Figure 5:
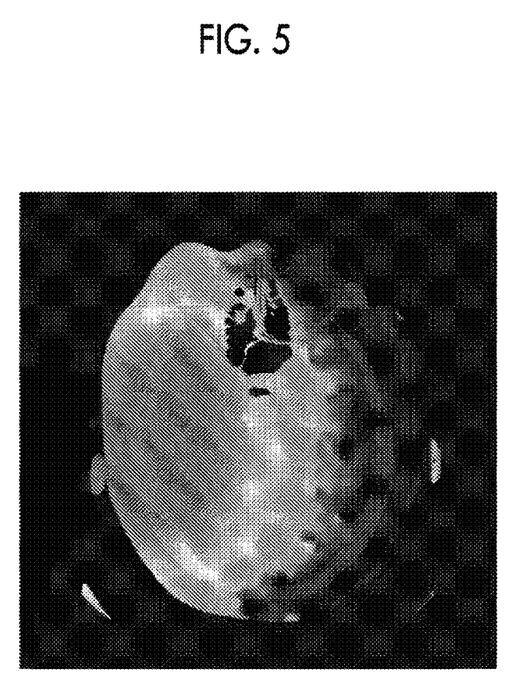
FIG. 5 is data indicating a distribution of neutron flux acquired when treatment is planned.

For example, the system configuration illustrated in FIG. 3 or the procedures of the treatment method illustrated in FIG. 4 are only examples, and all configurations and procedures may be employed within the scope of the concept of the present invention.

For example, in the embodiment, a device such as the controller 60 determines whether or not a calculated neutron beam distribution is obtained as planned for treatment (whether or not a calculated neutron beam distribution is within a predetermined range). Alternatively, a doctor or the like may perform the determination.

In the embodiment, the mechanism using the accelerator 11 and the target 8 is used as a mechanism for generating neutron beams. Alternatively, a configuration of directly generating neutron beams by using a reactor may be employed.

It should be understood that the invention is not limited to the above-described embodiment, but may be modified into various forms on the basis of the spirit of the invention. Additionally, the modifications are included in the scope of the invention.

What is claimed is:

1. A neutron capture therapy system comprising:
   a neutron beam irradiation unit that applies neutron beams;
   a treatment table on which an irradiation object irradiated with the neutron beams is mounted;
   a storage unit that stores distribution data indicating a distribution of hydrogen atoms or nitrogen atoms of a part to be irradiated of the irradiation object;
   a gamma ray detection unit that detects gamma rays generated from the irradiation object due to irradiation with the neutron beams; and
   a neutron flux distribution calculation unit that calculates a distribution of neutron flux in the irradiation object on the basis of the distribution data stored in the storage unit and gamma ray distribution data detected by the gamma ray detection unit.

2. The neutron capture therapy system according to claim 1, wherein the gamma ray detection unit is formed of a plurality of cameras, and
   wherein axes of the plurality of cameras intersect each other.

3. The neutron capture therapy system according to claim 1, wherein, in a case where a distribution of neutron flux calculated by the neutron flux distribution calculation unit has changed to exceed a range which is predefined on the basis of a distribution of neutron flux set in a treatment plan, the neutron beam irradiation unit stops irradiation with the neutron beams.

4. The neutron capture therapy system according to claim 1, further comprising:
   a display unit that displays a distribution of neutron flux calculated by the neutron flux distribution calculation unit.

* * * * *